(12) United States Patent
Mitov

(10) Patent No.: US 7,670,046 B2
(45) Date of Patent: Mar. 2, 2010

(54) FILLED HOTWIRE ELEMENTS AND SENSORS FOR THERMAL CONDUCTIVITY DETECTORS

(76) Inventor: Iliya Mitov, Tzar Alexander II Str., 23-B Apt. 16, Vidin (BG) 3700

( * ) Notice: Subject to any disclaimer, the term of this patent is extended or adjusted under 35 U.S.C. 154(b) by 219 days.

(21) Appl. No.: 11/978,312

(22) Filed: Oct. 29, 2007

(65) Prior Publication Data

US 2008/0310477 A1    Dec. 18, 2008

(30) Foreign Application Priority Data

Jun. 18, 2007    (BG) .................................... 109895

(51) Int. Cl.
*G01N 7/10* (2006.01)
*G01N 25/18* (2006.01)

(52) U.S. Cl. ..................... 374/44; 374/29; 73/25.03; 73/75; 436/149

(58) Field of Classification Search ........... 374/29, 374/100, 43, 44, 45, 137, 30–31, 35, 37, 374/208, 4, 5; 338/22 R, 28, 25; 436/149; 422/51
See application file for complete search history.

(56) References Cited

U.S. PATENT DOCUMENTS

| | | | | | |
|---|---|---|---|---|---|
| 1,698,887 | A | * | 1/1929 | Krueger | 73/25.03 |
| 1,741,231 | A | * | 12/1929 | Grondahl | 338/24 |
| 2,045,640 | A | * | 6/1936 | Fredericks | 73/25.03 |
| 2,888,330 | A | * | 5/1959 | Kapff | 436/141 |
| 3,201,990 | A | * | 8/1965 | Wald | 374/116 |
| 3,263,485 | A | * | 8/1966 | Mahmoodi | 374/44 |
| 3,478,574 | A | * | 11/1969 | Modell | 73/25.03 |
| 3,603,134 | A | * | 9/1971 | Norem | 73/25.04 |
| 3,959,764 | A | * | 5/1976 | Allman | 338/34 |
| 4,215,564 | A | | 8/1980 | Lawson et al. | |
| 4,254,654 | A | | 3/1981 | Clauser et al. | |
| 4,312,213 | A | * | 1/1982 | Schlau | 73/25.03 |
| 4,398,169 | A | * | 8/1983 | Hayashi | 338/25 |

(Continued)

FOREIGN PATENT DOCUMENTS

JP        55107944 A  *  8/1980

OTHER PUBLICATIONS

Mitov, I.P. And Petrov, L. A., Assensment of some possibilities for improving the performance of gas chromatography, Journal of Chromatography A, 715 (1995), 287-297.

(Continued)

*Primary Examiner*—Gail Verbitsky
(74) *Attorney, Agent, or Firm*—Michael Coblenz

(57) ABSTRACT

Hotwire element for thermal conductivity detectors, that comprises one or two individual nickel filaments each having resistance of above 200 ohm at 20° C. and an insulation coating of polytetrafluoroethylene with a thickness less than 5 micrometers, that are wound into a uniformly filled spherical or cylindrical body that has at least 33% gas-permeable hollow volume. Relevant hotwire sensor for thermal conductivity detectors, that comprises a wound on a centering holder filled element enveloped by fixed fillers forming a symmetric to it built-in cavity with an inlet and a gas outlet surrounding the centering holder. Radii of the filled elements and their cavities are in proportion, at which minimum electric current is needed for heating the elements to desired temperature.

4 Claims, 4 Drawing Sheets

U.S. PATENT DOCUMENTS

| | | | |
|---|---|---|---|
| 4,513,615 A * | 4/1985 | Sato et al. | 73/204.25 |
| 4,586,246 A * | 5/1986 | Oskoui | 29/612 |
| 4,735,082 A | 4/1988 | Kolloff | |
| 4,850,714 A * | 7/1989 | Wiegleb | 374/44 |
| 5,066,852 A * | 11/1991 | Willbanks | 219/544 |
| 5,265,459 A | 11/1993 | Cohen | |
| 5,300,916 A * | 4/1994 | Ishiguro et al. | 338/25 |
| 5,356,819 A * | 10/1994 | Ritschel | 436/147 |
| 5,756,878 A * | 5/1998 | Muto et al. | 73/25.03 |
| 6,085,588 A * | 7/2000 | Khadkikar et al. | 73/204.27 |
| 6,186,661 B1 * | 2/2001 | Hevey et al. | 374/29 |
| 6,550,961 B1 * | 4/2003 | Ueda | 374/44 |
| 6,688,159 B1 | 2/2004 | Grunewald | |
| 6,896,406 B2 * | 5/2005 | Gellert | 374/44 |
| 6,928,858 B2 * | 8/2005 | Lin | 73/25.03 |
| 7,452,126 B2 * | 11/2008 | Arndt et al. | 374/44 |
| 7,458,718 B2 * | 12/2008 | Krishnamurthy et al. | 374/208 |
| 2002/0135454 A1 * | 9/2002 | Ichida et al. | 338/25 |
| 2007/0169541 A1 * | 7/2007 | Norbeck et al. | 73/25.03 |
| 2007/0223558 A1 * | 9/2007 | Lopez et al. | 374/44 |
| 2008/0210002 A1 * | 9/2008 | Kamiunten et al. | 73/204.23 |
| 2009/0120162 A1 * | 5/2009 | Pratt | 73/23.31 |

OTHER PUBLICATIONS

GOW-MAC Instruments Co., GOW-MAC Detectors for Gas Analysis and Gas Chromatography, Sales Bulletine SB-10, Bethlehem, PA.
GOW-MAC Instruments Co., Thermal Conductivity Elements for Gas Analysis, Sales Bulletine SB-13, Bethlehem, PA.

* cited by examiner

FILLED HOTWIRE ELEMENTS AND SENSORS FOR THERMAL CONDUCTIVITY DETECTORS

CROSS REFERENCE TO RELATED APPLICATIONS

This application claims priority to Bulgarian patent application No. 109895, filed on Jun. 18, 2007.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC

Not Applicable.

BACKGROUND OF THE INVENTION

1. Field of the Invention

The present invention relates to thermal conductivity detectors used in gas chromatography and other methods for analysis and measurement of vaporous substances.

2. Description of the Related Art

The thermal conductivity detectors (often described by the initials TCD) follow differential approach and use one, two or four heated elements set in cavities with isothermal walls, through which sample and reference gas can flow. Common elements are thermistors (glass-coated beads of metal oxides) and hotwires (straight or spiral filaments fabricated from tungsten or nickel). Because their utilization requires proper installation, usually these elements are spot welded on the leads of replaceable sensors set in cavities bored into a massive metal block with constant temperature.

Owing to their sizable resistance (about 500 ohm in action) and temperature coefficient of resistivity, the thermistors have very good sensitivity despite their relatively thick coating. They are compact and suit the low volume cavities requisite for capillary gas chromatography. However, the selection of matched pairs of thermistors for the widely used Wheatstone bridge is rather difficult. Additionally, the thermistors should not be used in hydrogen atmosphere and can operate only below 100° C.

The hotwires cover the higher temperatures needed to analyze samples with boiling points of up to 250° C., but have moderate sensitivity due to their lower resistances (10 to 70 ohm at 20° C.) and temperature coefficients of resistivity. Since the hotwires wear out relatively fast, experiments were made to insulate them with PTFE (polytetrafluoroethylene, known under the trademark Teflon® of DuPont®), however unsatisfactory poor sensitivities were obtained using filaments with low resistances and thick coatings.

The hotwires are easier to match and also allow miniaturization, but quite large cavities are necessary for the widespread replaceable sensors with spiral filaments. The performance of these sensors can be improved using elements with resistance up to 800-1000 ohm and designs, at which the filaments heated by constant electric current have maximum temperature, however the spirals of increased sizes require cavities exceeding the volume suitable for capillary gas chromatography.

What is needed for improving the conventional thermal conductivity detectors (TCD) are highly sensitive, stable in wide enough temperature range, matchable and compact elements and relevant low volume and fast responding TCD sensors with optimized performance.

BRIEF SUMMARY OF THE INVENTION

According to the present invention, the element for thermal conductivity detectors comprises one or two individual filaments each having resistance of above 200 ohm at 20° C. and an insulation coating with a thickness less than 5 micrometers, that are loosely wound into a uniformly filled body that has at least 33% gas-permeable hollow volume and constant local density at each 1% volumetric partition. Actual highly sensitive and stable in wide enough temperature range filled elements are created using commercially available nickel filaments with PTFE coating. These elements can be quite easily matched in pairs or quads and are very compact, especially the combined filled elements each comprising two individual filaments, designed for the most widely used thermal conductivity detectors with four filaments in a Wheatstone bridge. Due to their gas-permeable hollow volume the disclosed filled elements are not retentive and have response that is suitable for the relevant low volume direct flow-through cavities.

The embodiments of the disclosed filled elements into TCD sensors, preferred to lighter designs without auxiliary components, better utilize the intrinsic performance of these elements and the essential finding that the heating of filled spherical or cylindrical elements to desired temperature requires minimum electric current, if the radii of their cavities are approximately 1.5 or 1.65 times larger than the radius of the respective filled element.

To realize these optimum proportions in lower volume, the disclosed relevant TCD sensors have fixed fillers forming a built-in cavity with an inlet and an a gas outlet surrounding the centering holder used to fix the filled elements in their cavities. Besides the actual filled elements have radii accordant with a uniform cavity radius of 1.6 mm. This unification facilitates the manufacturing of inwardly spherical TCD sensors with two individual filaments each of resistance 450 ohm at 20° C. and suited for the capillary gas chromatography void volume below 15 mm$^3$ ensuring fast response, and of more vigorous inwardly cylindrical sensors with higher resistances and increased volumes.

In addition to their high sensitivity the disclosed filled TCD sensors also have very low detection limits, since the heat conduction through the centering holder that is surrounded by the gas outlet of the build-in cavity counterbalances the interferences caused by gas flow fluctuations.

DETAILED DESCRIPTION OF THE INVENTION

Figure 1:
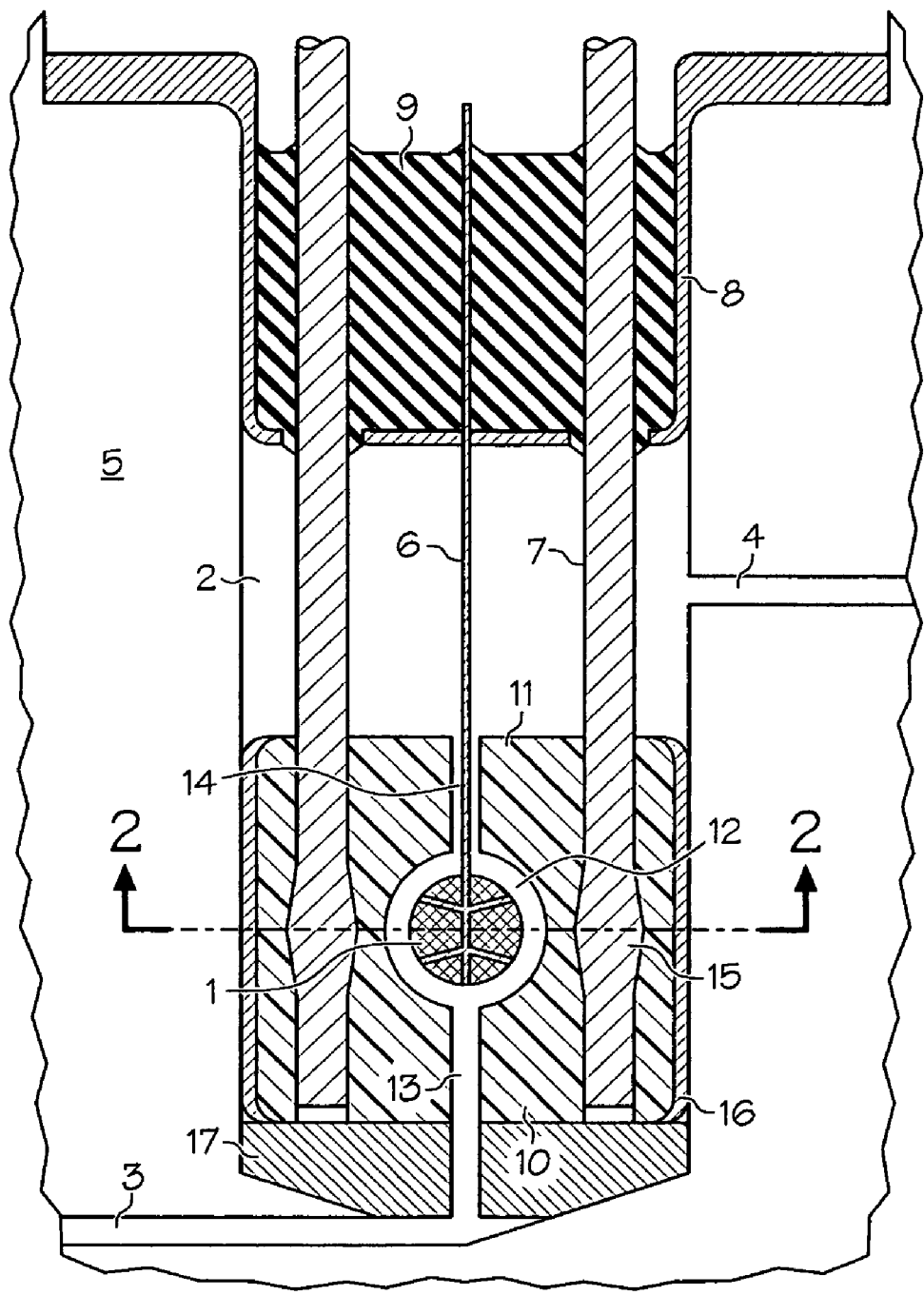
FIG. 1 represents axial section of a relevant sensor comprising spherical filled element, set in a cell of the detector block.

Two unified embodiments of the invention are presented respectively in FIG. 1, 2 and FIG. 3, 4, 5. FIG. 1 depicts an axial section of a relevant TCD sensor comprising a spherical filled element 1, set in a cell 2 bored together with its inlet 3 and outlet 4 into the detector block 5. The spherical filled element 1 is created by winding of one or two individual filaments 25 (illustrated in FIG. 5) on a centering holder 6, further fixed together with four leads 7 in the sensor base 8 by a glass seal 9. Using nickel filaments of radius 12 micrometers with 2 micrometers thick PTFE coating, both individual filaments 25 in a combined spherical filled element 1 of radius 1.1 mm and 33% gas-permeable hollow volume have resistance 450 ohm at 20° C. Slight differences in their resistances are not critical because the matching concerns the filaments of separate TCD sensors set in the reference and sample gas cavities. Larger selection is needed to match the disclosed composite TCD sensors, but the fact that their two individual filaments 25 always have equal temperature ensures more stable balance of the Wheatstone bridge.

The spherical filled element 1 is enveloped by PTFE fillers 10 and 11 forming a symmetric to it build-in cavity 12 with void volume of 13.5 mm$^3$, an inlet 13 and a gas outlet 14 surrounding the centering holder 6. The PTFE fillers 10 and 11 are fixed using the flattened segments 15 of the leads 7 and a metal casing 16. Accessory filler 17 reduces the operative detector volume and augments the thermal contacts keeping the walls of the build-in cavity 12 at constant temperature.

Figure 2:
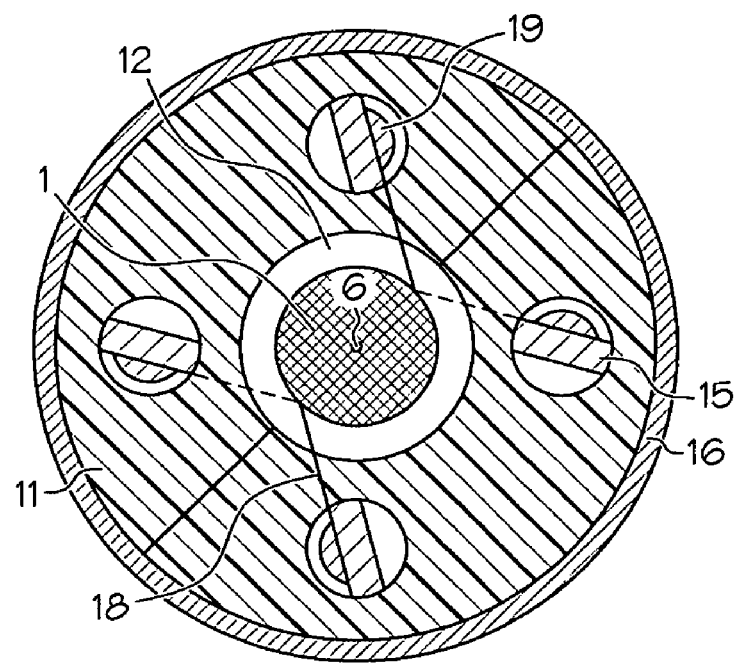
FIG. 2 represents cross-section 2-2 marked in FIG. 1.

FIG. 2 represents cross-section 2-2 marked in FIG. 1. In this plane between the PTFE fillers 10 and 11 the filament ends 18 are connected to the flattened segments 15 of the leads 7 by spot welds 19. Since the welding destroys the adjacent PTFE coating, during this operation the filament ends 18 are kept slack and then tightly pressed by the PTFE fillers 10 and 11 to obtain a TCD sensor with fully insulated filaments. In FIG. 2 two filament ends 18 are depicted by dashed lines to notice that in the disclosed TCD sensors comprising a spherical filled element 1 with a single filament 25 of resistance twice the aforesaid 450 ohm at 20° C. two leads 7 are not connected electrically. Outside the sensor base 8 presented in FIG. 1 such leads 7 are cut like the centering holder 6. In all other aspects the single-filament filled TCD sensors are identical to the respective composite sensors with two individual filaments 25 externally connected in series. FIG. 2 also shows that (in order to realize the sensors assembling described below) the PTFE filler 11 is axially slit in two parts.

Figure 3:
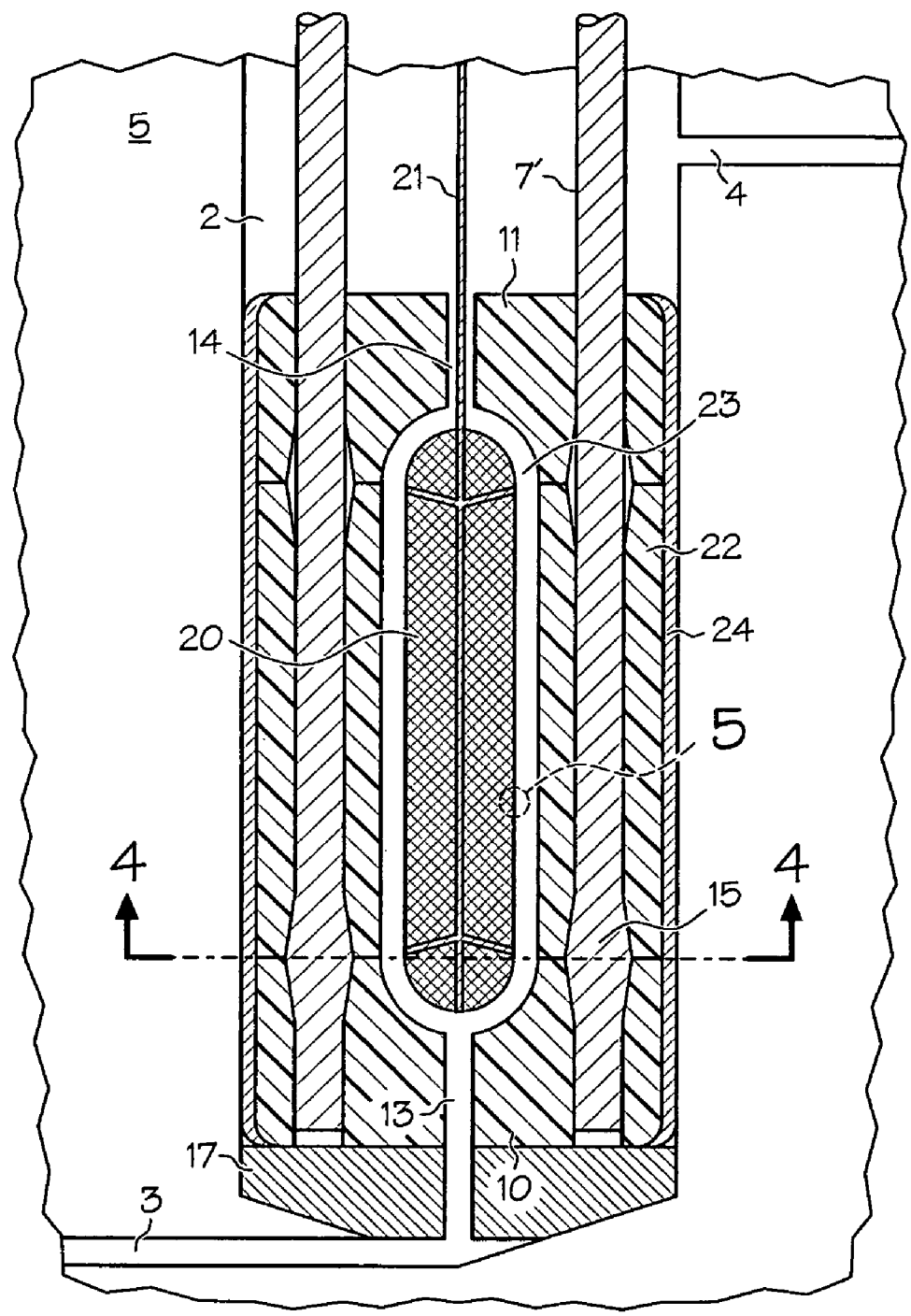
FIG. 3 represents in axial section main portion of a relevant sensor comprising cylindrical filled element, set in a cell of the detector block.

FIG. 3 represents in axial section the main portion of a relevant TCD sensor comprising a cylindrical filled element 20 created by winding of two individual filaments 25 on a centering holder 21. Due to the unification many details in FIG. 3 and FIG. 1 are identical or very similar and therefore have the same or primed numbers. Also for this reason the sensor portion above the outlet 4 is skipped in FIG. 3. Using the aforesaid materials and extent of filling, both individual filaments 25 in a combined cylindrical filled element 20 of radius 1.0 mm, length about 11 mm and 33% gas-permeable hollow volume have resistance 2870 ohm at 20° C.

The cylindrical filled element 20 is enveloped by PTFE fillers 10, 11 and 22 forming a symmetric to it build-in cavity 23 with void volume of 74.5 mm$^3$, an inlet 13 and a gas outlet 14 surrounding the centering holder 21. The PTFE fillers 10, 11 and 22 are fixed using the flattened segments 15 of the leads 7' and a metal casing 24.

Figure 4:
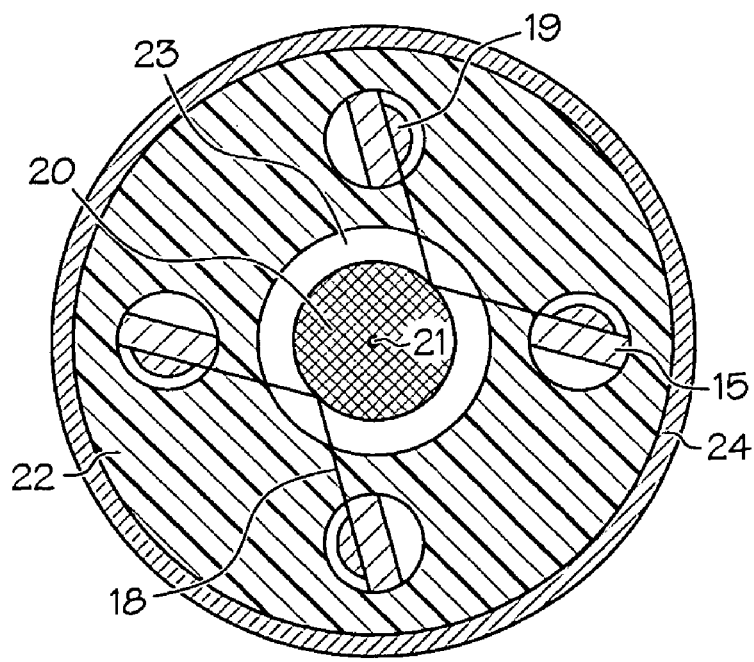
FIG. 4 represents cross-section 4-4 marked in FIG. 3.

FIG. 4 represents cross-section 4-4 marked in FIG. 3. In this plane the filament ends 18 are connected to the flattened segments 15 of the leads 7' by the spot welds 19 and then tightly pressed by the PTFE fillers 10, 11 and 22 to obtain a TCD sensor with fully insulated filaments.

Figure 5:
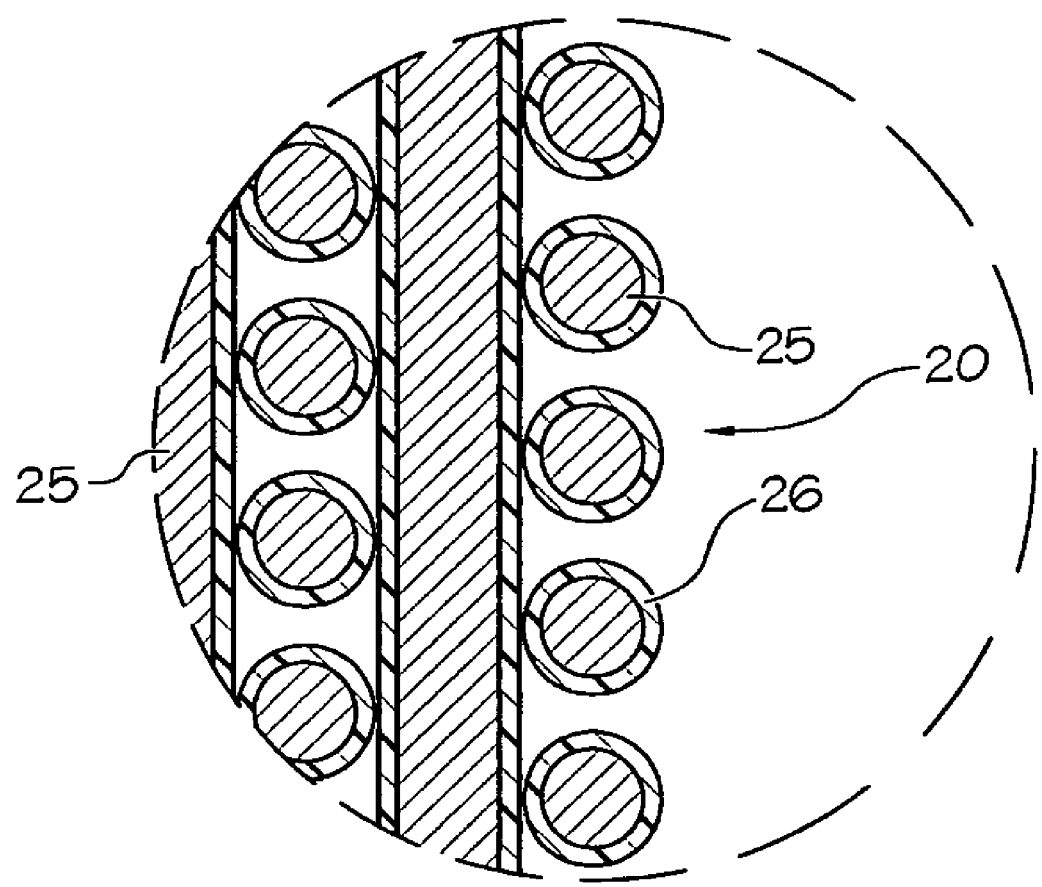
FIG. 5 represents a detailed partial view 5 marked in FIG. 3.

FIG. 5 represents detailed partial view 5 of the cylindrical filled element 20 shown in FIG. 3 and illustrates how in this instance two individual nickel filaments 25 with PTFE coating 26 are loosely wound into a uniformly filled body that has at least 33% gas-permeable volume.

The sensors assembling begins with mechanized winding of one or two individual filaments 25 into a spherical filled element 1 or a cylindrical filled element 20 on the respective centering holders 6 and 21, which constituents are originally longer to facilitate the work. The desired 33% gas-permeable hollow volume of each spherical filled element 1 or cylindrical filled element 20 is obtained by applying only slight tension to its one or two individual filaments 25 during their spaced winding into a uniformly filled body that is illustrated in FIG. 5. To stabilize each spherical filled element 1 or cylindrical filled element 20, the endmost portions of its one or two individual filaments 25 are run through it several times using a fine needle. After pruning of their prongs the centering holders 6 or 21 and four leads 7 or 7' are fixed in the sensor base 8 by the glass seal 9. Then the two parts of the PTFE filler 11 are one at a time put on the leads 7 or 7' up to the sensor base 8 by deflecting the spherical filled element 1 or the cylindrical filled element 20 in the respective opposite direction. In the disclosed inwardly cylindrical TCD sensors the PTFE filler 22 is put on the leads 7' near the PTFE filler 11. At the assembling finish the tag of the centering holders 6 and 21 is also pruned, the segments 15 of the leads 7 or 7' are flattened, the filament ends 18 are spot welded there and finally the PTFE fillers 10, 11 and in case 22 are fixed using the flattened segments 15 of the leads 7 or 7' and the fitting one of the metal casings 16 or 24, which edges are lastly bent.

From the above description of the preferred embodiments, those skilled in the art will not only understand the invention and its advantages, but will also find apparent various changes of the disclosed filled hotwire elements and sensors for thermal conductivity detectors. Therefore it is sought to cover all such modifications as falling within the spirit and scope of the present invention defined by the appended claims.

What is claimed is:

1. An element for thermal conductivity detectors having insulated hotwires,
    the element comprising one or two individual filaments,
    wherein each of said one or two individual filaments has resistance of above 200 ohm at 20° C.,
    wherein each of said one or two individual filaments has an insulation coating with a thickness less than 5 micrometers, and
    wherein said one or two individual filaments are wound into a uniformly filled body that has at least 33% gas-permeable hollow volume and constant local density at each 1% volumetric partition.

2. A sensor for thermal conductivity detectors having insulated with polytetrafluoroethylene coating nickel hotwires, spot welded to leads that are sealed together with a centering holder in a base and fixed fillers forming a build-in cavity with an inlet and a gas outlet,
    the sensor comprising an element as set forth in claim 1,
    wherein said one or two individual filaments are wound into said uniformly filled body on said centering holder that passes through said gas outlet of said built-in cavity.

3. A sensor as set forth in claim 2,
    wherein said built-in cavity and said element are spherical and the radius of said built-in cavity is approximately 1.5 times larger than the radius of said element.

4. A sensor as set forth in claim 2,
    wherein said built-in cavity and said element are cylindrical and the radius of said built-in cavity is approximately 1.65 times larger than the radius of said element.

* * * * *